United States Patent
Penna

(10) Patent No.: US 9,204,881 B2
(45) Date of Patent: Dec. 8, 2015

(54) BUTTRESS RETAINER FOR EEA ANVIL

(71) Applicant: Covidien LP, Mansfield, MA (US)

(72) Inventor: Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 486 days.

(21) Appl. No.: 13/739,226

(22) Filed: Jan. 11, 2013

(65) Prior Publication Data

US 2014/0197224 A1    Jul. 17, 2014

(51) Int. Cl.
*A61B 17/072* (2006.01)
*A61B 17/115* (2006.01)

(52) U.S. Cl.
CPC ....... *A61B 17/1155* (2013.01); *A61B 17/07292* (2013.01); *A61B 17/115* (2013.01)

(58) Field of Classification Search
CPC . A61B 17/1155; A61B 17/072; A61B 17/068
USPC ............. 227/176.1, 178.1, 179.1, 180, 181.1; 606/219
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,490,675 A | 1/1970 | Green et al. |
| 3,499,591 A | 3/1970 | Green |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,473,077 A | 9/1984 | Noiles et al. |
| 4,576,167 A | 3/1986 | Noiles |
| 4,605,730 A | 8/1986 | Shalaby et al. |
| 4,646,745 A | 3/1987 | Noiles |

(Continued)

FOREIGN PATENT DOCUMENTS

| | | |
|---|---|---|
| CA | 2 667 434 | 5/2008 |
| DE | 1 99 24 311 A1 | 11/2000 |

(Continued)

OTHER PUBLICATIONS

Extended European Search Report corresponding to EP 12 19 1035.0, completed Jan. 11, 2013 and mailed Jan. 18, 2013; 7 pages.

(Continued)

*Primary Examiner* — Nathaniel Chukwurah

(57) ABSTRACT

An apparatus for joining two hollow organ sections with an annular array of staples includes a staple cartridge assembly, an anvil assembly, and a buttress assembly. The staple cartridge assembly includes a plurality of surgical staples in an annular array. The anvil assembly includes an anvil member and a shaft extending therefrom. The anvil member defines a plurality of staple pockets for deforming the staples. The anvil assembly is movable relative to the staple cartridge assembly between spaced apart and approximated positions to adjustably clamp tissue between the staple cartridge and the anvil assemblies. The buttress assembly includes a cut ring secured with the anvil member, a buttress member disposed in a superposed relation with the plurality of staple pockets defined in the anvil member, and a retaining member having an attaching member configured to be secured with the cut ring to secure the buttress member with the anvil assembly.

18 Claims, 4 Drawing Sheets

(56) References Cited

U.S. PATENT DOCUMENTS

| | | |
|---|---|---|
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,005,749 A | 4/1991 | Aranyi |
| 5,014,899 A | 5/1991 | Presty et al. |
| 5,040,715 A | 8/1991 | Green et al. |
| 5,065,929 A | 11/1991 | Schulze et al. |
| 5,119,983 A | 6/1992 | Green et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,588,579 A * | 12/1996 | Schnut et al. ............... 227/175.1 |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,053,390 A | 4/2000 | Green et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,748 B2 | 10/2006 | Mooradian et al. |
| 7,141,055 B2 | 11/2006 | Abrams et al. |
| 7,147,138 B2 | 12/2006 | Shelton, IV |
| 7,160,299 B2 | 1/2007 | Baily |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Bettuchi et al. |
| 7,722,642 B2 | 5/2010 | Williamson, IV |
| 7,744,627 B2 | 6/2010 | Orban, III et al. |
| 7,776,060 B2 | 8/2010 | Mooradian |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crows et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,016,177 B2 | 9/2011 | Bettuchi |
| 8,016,178 B2 | 9/2011 | Olson |
| 8,028,883 B2 | 10/2011 | Stopek |
| 8,062,330 B2 | 11/2011 | Prommersberger |
| 8,083,119 B2 | 12/2011 | Prommersberger |
| 8,123,766 B2 | 2/2012 | Bauman |
| 8,123,767 B2 | 2/2012 | Bauman |
| 8,146,791 B2 | 4/2012 | Bettuchi |
| 8,157,149 B2 | 4/2012 | Olson |
| 8,157,151 B2 | 4/2012 | Ingmanson |

(56) References Cited

U.S. PATENT DOCUMENTS

| | | |
|---|---|---|
| 8,167,895 B2 | 5/2012 | D'Agostino |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,668,129 B2 | 3/2014 | Olson |
| 8,684,250 B2 | 4/2014 | Bettuchi |
| 8,757,466 B2 | 6/2014 | Olson |
| 8,789,737 B2 | 7/2014 | Hodgkinson |
| 8,820,606 B2 | 9/2014 | Hodgkinson |
| 8,870,050 B2 | 10/2014 | Hodgkinson |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 2002/0028243 A1 | 3/2002 | Masters |
| 2002/0091397 A1 | 7/2002 | Chen |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2006/0004407 A1 | 1/2006 | Hiles et al. |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016888 A1 | 1/2010 | Calabrese et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |

(56) References Cited

U.S. PATENT DOCUMENTS

| | | |
|---|---|---|
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0215132 A1 | 9/2011 | Aranyi |
| 2012/0074199 A1 | 3/2012 | Olson |
| 2012/0080336 A1 | 4/2012 | Shelton |
| 2012/0187179 A1 | 7/2012 | Gleiman |
| 2012/0241499 A1 | 9/2012 | Baxter |
| 2012/0273547 A1 | 11/2012 | Hodgkinson et al. |
| 2012/0298721 A1* | 11/2012 | Bettuchi et al. ............ 227/176.1 |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0277411 A1 | 10/2013 | Hodgkinson |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | (Prommersberger) Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |

FOREIGN PATENT DOCUMENTS

| | | |
|---|---|---|
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 256 318 | 11/2002 |
| EP | 1 621 141 A2 | 2/2006 |
| EP | 1 520 525 A1 | 4/2006 |
| EP | 1 702 570 A2 | 9/2006 |
| EP | 1 759 640 A2 | 3/2007 |
| EP | 1 815 804 A2 | 8/2007 |
| EP | 1 825 820 | 8/2007 |
| EP | 1 929 958 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 | 8/2009 |
| EP | 2 090 244 | 8/2009 |
| EP | 2 090 252 | 8/2009 |
| EP | 2163211 A2 | 3/2010 |
| EP | 2189121 A1 | 5/2010 |
| EP | 2 198 787 A1 | 6/2010 |
| EP | 2 236 098 A2 | 10/2010 |
| EP | 2 236 099 | 10/2010 |
| EP | 2258282 A2 | 12/2010 |
| EP | 2 292 276 A2 | 3/2011 |
| EP | 2 311 386 | 4/2011 |
| EP | 2 436 348 | 4/2012 |
| EP | 2 462 880 | 6/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 105 A1 | 7/2013 |
| EP | 2 620 106 | 7/2013 |
| EP | 2 630 922 | 8/2013 |
| EP | 2 644 125 | 10/2013 |
| EP | 2 762 091 A2 | 8/2014 |
| JP | 2000-166933 | 6/2000 |
| JP | 2002-202213 | 7/2002 |
| JP | 2007/124166 | 5/2007 |
| WO | WO 90/05489 A1 | 5/1990 |
| WO | WO 95/16221 | 6/1995 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |
| WO | WO 03/088845 | 10/2003 |
| WO | WO 03/094743 | 11/2003 |
| WO | Wo 03/105698 A2 | 12/2003 |
| WO | WO 2005/079675 | 9/2005 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

Extended European Search Report corresponding to EP 12 19 6904. 2, completed Mar. 28, 2013 and mailed Jul. 26, 2013; 8 pages.

Extended European Search Report corresponding to EP 12 19 8749. 9, completed May 21, 2013 and mailed May 31, 2013; 8 pages.

Extended European Search Report corresponding to EP 07 00 5842. 5, completed May 13, 2013 and mailed May 29, 2013; 7 pages.

Extended European Search Report corresponding to EP 12 19 8776. 2, completed May 16, 2013 and mailed May 27, 2013; 8 pages.

Extended European Search Report corresponding to EP 13 15 6297. 7, completed Jun. 4, 2013 and mailed Jun. 13, 2013; 7 pages.

(56) References Cited

OTHER PUBLICATIONS

Extended European Search Report corresponding to EP 13 17 3885.6, completed Aug. 19, 2013 and mailed Aug. 28, 2013; 6 pages.
Extended European Search Report corresponding to EP 13 17 3986.4, completed Aug. 20, 2013 and mailed Aug. 29, 2013; 7 pages.
Extended European Search Report corresponding to EP 13 17 7437.4, completed Sep. 11, 2013 and mailed Sep. 19, 2013; (6 pp).
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).
Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).
Extended European Search Report corresponding to EP No. 12 19 1035.0, completed Jan. 11, 2013 and mailed Jan. 18, 2013; 7 pages.
Extended European Search Report corresponding to EP No. 12 18 6175.1, completed Jan. 15, 2013 and mailed Jan. 23, 2013; 7 pages.
Extended European Search Report corresponding to EP No. 12 19 1114.3, completed Jan. 23, 2013 and mailed Jan. 31, 2013; 10 pages.
Extended European Search Report corresponding to EP No. 12 19 2224.9, completed Mar. 14, 2013 and mailed Mar. 26, 2013; 8 pages.
Extended European Search Report corresponding to EP No. 12 19 6911.7, completed Apr. 18, 2013 and mailed Apr. 24, 2013; 8 pages.
Extended European Search Report corresponding to EP 08 72 6500.5, completed Feb. 20, 2014 and mailed Mar. 3, 2014; (7 pp).
Extended European Search Report corresponding to EP 13 19 5919.9, completed Feb. 10, 2014 and mailed Mar. 3, 2014; (7 pp).
Extended European Search Report corresponding to EP 13 19 2123.1, completed Jan. 30, 2014 and mailed Feb. 10, 2014; (8 pp).
Extended European Search Report corresponding to EP 13 19 6816.6, completed Mar. 28, 2014 and mailed Apr. 9, 2014; (9 pp).
Extended European Search Report corresponding to EP 13 19 4995.0, completed Jun. 5, 2014 and mailed Jun. 16, 2014; (5 pp).
Extended European Search Report corresponding to EP 13 19 5019.8, completed Mar. 14, 2014 and mailed Mar. 24, 2014; (7 pp).
Extended European Search Report corresponding to EP 13 19 2111.6, completed Feb. 13, 2014 and mailed Feb. 27, 2014; (10 pp).
Extended European Search Report corresponding to EP 13 19 7958.5, completed Apr. 4, 2014 and mailed Apr. 15, 2014; (8 pp).
Extended European Search Report corresponding to EP 14 15 6342.9, completed Jul. 22, 2014 and mailed Jul. 29, 2014; (8 pp).
Extended European Search Report corresponding to EP 14 15 7195.0, completed Jun. 5, 2014 and mailed Jun. 18, 2014; (9 pp).
International Search Report corresponding to European Application No. EP 05 02 2585.3, completed on Jan. 25, 2006 and mailed on Feb. 3, 2006; 4 pages.
International Search Report corresponding to European Application No. EP 06 00 4598, completed on Jun. 22, 2006; 2 pages.
International Search Report corresponding to European Application No. EP 06 01 6962.0, completed on Jan. 3, 2007 and mailed on Jan. 11, 2007; 10 pages.
International Search Report corresponding to International Application No. PCT/US05/36740, completed on Feb. 20, 2007 and mailed on Mar. 23, 2007; 8 pages.
International Search Report corresponding to International Application No. PCT/US2007/022713, completed on Apr. 21, 2008 and mailed on May 15, 2008; 1 page.
International Search Report corresponding to International Application No. PCT/US2008/002981, completed on Jun. 9, 2008 and mailed on Jun. 26, 2008; 2 pages.
International Search Report corresponding to European Application No. EP 08 25 1779, completed on Jul. 14, 2008 and mailed on Jul. 23, 2008; 5 pages.
International Search Report corresponding to European Application No. EP 08 25 1989.3, completed on Mar. 11, 2010 and mailed on Mar. 24, 2010; 6 pages.
International Search Report corresponding to European Application No. EP 10 25 0639.1, completed on Jun. 17, 2010 and mailed on Jun. 28, 2010; 7 pages.
Copy of International Search Report corresponding to European Application No. EP 10 25 0715.9, completed on Jun. 30, 2010 and mailed on Jul. 20, 2010; 3 pages.
International Search Report corresponding to European Application No. EP 05 80 4382.9, completed on Oct. 5, 2010 and mailed on Oct. 12, 2010; 3 pages.
International Search Report corresponding to European Application No. EP 10 25 1437.9, completed on Nov. 22, 2010 and mailed on Dec. 16, 2010; 3 pages.
International Search Report corresponding to European Application No. EP 09 25 2897.5, completed on Feb. 7, 2011 and mailed on Feb. 15, 2011; 3 pages.
International Search Report corresponding to European Application No. EP 10 25 0642.5, completed on Mar. 25, 2011 and mailed on Apr. 4, 2011; 4 pages.
International Search Report corresponding to European Application No. EP 11 18 8309.6, completed Dec. 15, 2011 and mailed on Jan. 12, 2012; 3 pages.
International Search Report corresponding to European Application No. EP 12 15 2229.6, completed on Feb. 23, 2012 and mailed on Mar. 1, 2012; 4 pages.
International Search Report corresponding to European Application No. EP 12 15 0511.9, completed on Apr. 16, 2012 and mailed on Apr. 24, 2012; 7 pages.
International Search Report corresponding to European Application No. EP 12 15 2541.4, completed on Apr. 23, 2013 and mailed on May 3, 2012; 10 pages.
International Search Report corresponding to European Application No. EP 12 16 5609.4, completed on Jul. 5, 2012 and mailed on Jul. 13, 2012; 8 pages.
International Search Report corresponding to European Application No. EP 12 15 8861.0, completed on Jul. 17, 2012 and mailed on Jul. 24, 2012; 9 pages.
International Search Report corresponding to European Application No. EP 12 16 5878.5, completed on Jul. 24, 2012 and mailed on Aug. 6, 2012; 8 pages.
Extended European Search Report EP14150728.5-1654 dated Aug. 12, 2015.

\* cited by examiner

BUTTRESS RETAINER FOR EEA ANVIL

BACKGROUND

1. Technical Field

The present disclosure relates to a surgical instrument for applying surgical fasteners or staples to body tissue, and more particularly, to a surgical buttress assembly for use with an end-to-end anastomosis stapling apparatus.

2. Background of Related Art

Anastomosis is a surgical joining of separate hollow organ sections. Typically, an anastomosis procedure follows surgery in which a diseased or defective section of hollow tissue is removed and the remaining end sections are joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Typically, these instruments include an elongated shaft having a handle portion at a proximal end to actuate the instrument and a staple holding component disposed at a distal end. An anvil assembly including an anvil shaft with attached anvil head is mounted to the distal end adjacent the staple holding component. Opposed end sections of the organ to be stapled are clamped between the anvil head and the staple holding component. The clamped tissue is stapled by driving a plurality of staples from the staple holding component so that the ends of the staples pass through the tissue and are deformed by the anvil head.

In use, one end section of the organ is secured about the anvil assembly and the other end section of the organ is held in place adjacent the staple holding component. The shaft of the anvil assembly is removably connected to the instrument. Once the anvil shaft is secured to the instrument, the anvil is drawn into close approximation to the staple holding component. The instrument is then fired to cause the staples to pass through tissue of both sections of the organ and deform against the anvil. During the firing step, a circular knife is advanced to cut tissue inside the staple line, thereby establishing a passage between the two sections of the organ. After firing, the instrument is typically removed by withdrawing the anvil through the staple line, after which the surgeon will carefully inspect the surgical site to ensure a proper anastomosis has been achieved.

While circular staplers are helpful in a number of surgical procedures, complications such as anastomotic leak, tear of tissue during stapler extraction, bleeding, and other complications may arise. In order to remedy or reduce incidents of such complications, buttress or reinforcing materials have been utilized. However, due to inherent difficulties in positioning and securing such materials with the underlying surgical instrument, a need exists for a buttress material that can be safely and effectively positioned on an anvil assembly of the surgical instrument.

SUMMARY

In accordance with an embodiment of the present disclosure, there is provided an apparatus for joining two hollow organ sections with an annular array of surgical staples. The apparatus includes a staple cartridge assembly, an anvil assembly, and a buttress assembly. The staple cartridge assembly includes a plurality of surgical staples in an annular array. The anvil assembly includes an anvil member and a shaft extending therefrom. The anvil member includes a proximal surface defining a plurality of staple pockets for deforming the surgical staples. The anvil assembly is movable relative to the staple cartridge assembly between spaced apart and approximated positions to adjustably clamp tissue between the staple cartridge and anvil assemblies. The buttress assembly includes a cut ring configured to engage a knife member, a buttress member, and a retaining member. The cut ring is secured with the anvil member. The buttress member is disposed in a superposed relation with the plurality of staple pockets defined in the anvil member. The retaining member has an attaching member configured to be secured with the cut ring to secure the buttress member between the cut ring and the retaining member, and to position the buttress member relative to the anvil assembly.

In an embodiment, the proximal surface of the anvil member may further define a recess defined radially inward of the plurality of staple pockets. The recess may be configured and dimensioned to securely receive the cut ring therein. In particular, the cut ring may be configured to engage an inner wall of the recess to provide securement of the cut ring thereagainst.

In another embodiment, the buttress member may have an annular configuration. The buttress member may include a bore configured and dimensioned to receive the attaching member of the retaining member therethrough. The attaching member may be a boss extending distally from the retaining member.

In yet another embodiment, the cut ring may define a bore configured and dimensioned to receive the boss. The boss may be secured to the bores of the cut ring through heat staking. The cut ring may include a proximal face having a base portion and a raised portion extending proximally from the base portion. The raised portion may be configured and dimensioned to engage the knife member. In an embodiment, the raised portion may be substantially flush with the proximal surface of the anvil member. In addition, the raised portion may be disposed at a peripheral portion of the cut ring.

In still yet another embodiment, the retaining member may have an annular configuration. The retaining member may be in a superposed relation with the buttress member. The retaining member may be concentrically aligned with the anvil member. A radially outer peripheral portion of the buttress member may be flush with a peripheral edge of the anvil member. The retaining member may be configured to engage a proximal face of the buttress member. The buttress member may be made of a biodegradable material.

In still yet another embodiment, the knife member may be concentrically arranged with the plurality of surgical staples in the staple cartridge assembly. The knife member may be movable relative to the staple cartridge assembly, wherein the retaining member is disposed radially inward of the knife member when the knife member is actuated to engage the buttress member. The buttress member may be concentrically aligned with the plurality of staple pockets and may be interposed between the cut ring and the retaining member. The buttress member and the cut ring may be concentrically arranged with each other.

BRIEF DESCRIPTION OF THE DRAWINGS

Various embodiments of the present disclosure are described hereinbelow with reference to the drawings, wherein.

DETAILED DESCRIPTION OF EMBODIMENTS

Figure 1:
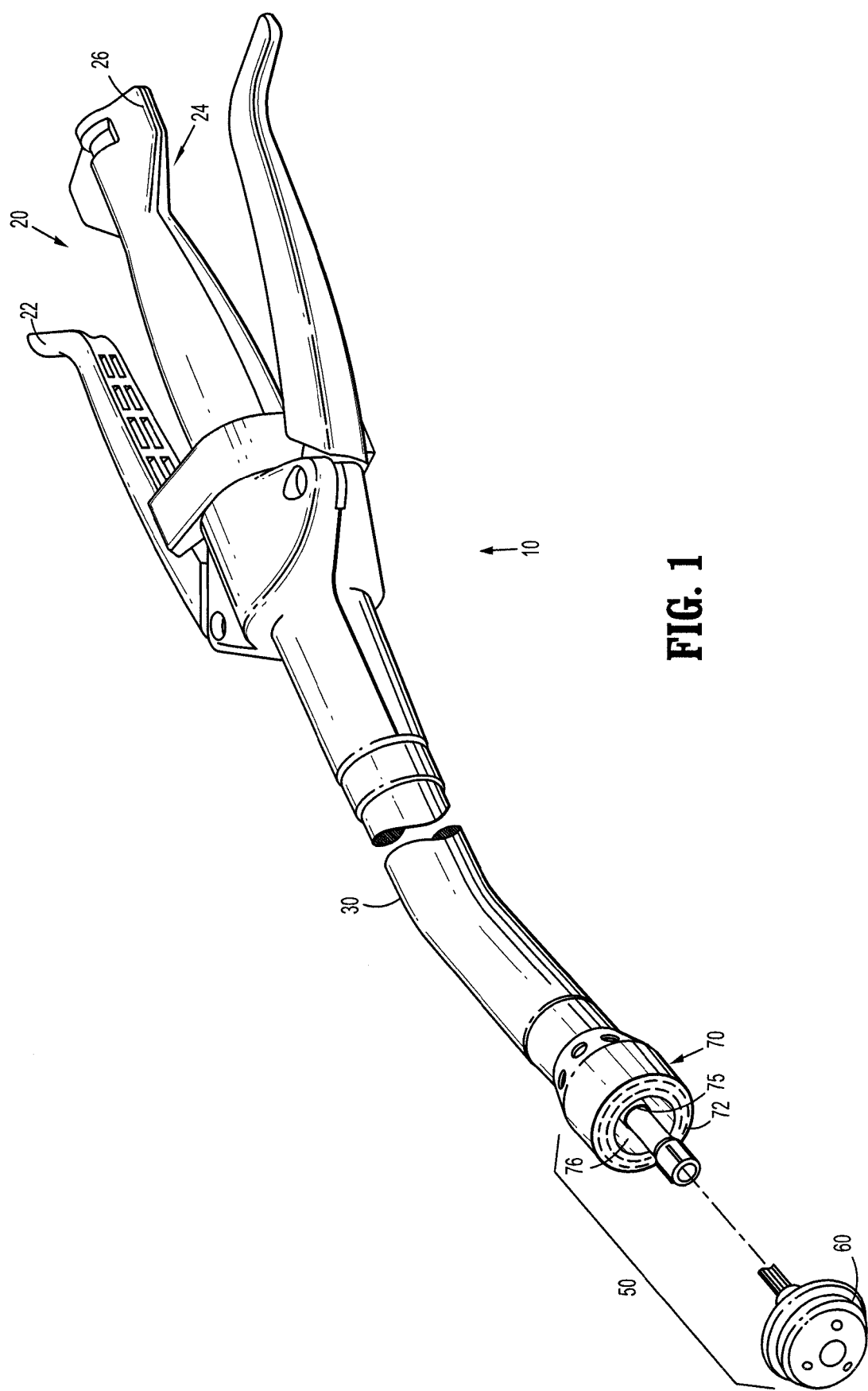
FIG. 1 is a perspective view of an annular surgical stapling apparatus configured for use with a surgical buttress assembly in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, a surgical stapling apparatus 10 for performing circular anastomosis of hollow organs is shown. Surgical stapling apparatus 10 drives a circular array of staples (not shown) through the end sections of each organ and simultaneously fires an cylindrical knife 76 to core any tissue interior of the driven circular array of staples to free the tubular passage, and thereby joining two ends of the organ. Surgical stapling apparatus 10 includes a handle assembly 20 having a pair of pivotable actuating handle members 22 and an advancing means 24 including a rotatable grip member 26, an elongate body portion 30 extending distally from handle assembly 20, and a head portion 50 including an anvil assembly 60, a staple cartridge assembly 70, and a surgical buttress assembly 100 (FIG. 3) in accordance with an embodiment of the present disclosure. The components of surgical stapling apparatus 10 are generally formed from thermoplastics including polycarbonates, and metals including stainless steel and aluminum. The particular material selected to form a particular component will depend upon the strength requirements of the particular component. The staples may be of a conventional type and may include a backspan having a pair of legs extending from the backspan. The legs terminate in tissue penetrating tips.

Handle assembly 20 can be actuated to approximate anvil assembly 60 relative to staple cartridge assembly 70 and to apply a pair of annular arrays of staples through tissue. In order to properly position tissue in head portion 50, rotatable grip member 26 may be rotated to move anvil assembly 60 axially relative to staple cartridge assembly 70 between a spaced apart position and an approximated position in which anvil assembly 60 is positioned adjacent staple cartridge assembly 70 to clamp tissue therebetween. Handle members 22 may be squeezed to fire the staples through tissue to join two segments "$T_1$," "$T_2$" (FIG. 5) of tubular tissues together, as will be discussed in detail below.

Elongate body portion 30 is constructed to have a slightly curved/bent shape along its length. However, elongate body portion 30 may also be straight, as well as flexible to bend to any configuration. The length, shape and/or the diameter of elongate body portion 30 may be varied to suit a particular surgical procedure.

With reference to FIGS. 1-4, head portion 50 includes a staple cartridge assembly 70, an anvil assembly 60, and a surgical buttress assembly 100 detachably secured with anvil assembly 60. Staple cartridge assembly 70 may be fixedly connected to a distal end portion of elongate body portion 30 or may be configured to concentrically fit within the distal end portion of elongate body portion 30. In particular, staple cartridge assembly 70 defines a pair of annular arrays of staple receiving slots 72 having a staple disposed in each one of staple receiving slots 72. In addition, staple cartridge assembly 70 includes a cylindrical knife 76 concentrically arranged with the pair of annular array of staples and a plurality of staple pushers (not shown) each disposed in staple receiving slot 72 to eject the staple through slot 72. The staples travel through slots 72 and tissue toward anvil assembly 60.

Cylindrical knife 76 includes a distal rim defining a knife blade adapted to cut tissue and portions of surgical buttress assembly 100. Upon actuation of handle members 22, cylindrical knife 76 is moved distally to cut tissue and portions of buttress member 110, and the plurality of pushers are moved distally to eject the staples disposed in staple receiving slots 72 therethrough, toward anvil assembly 60.

Figure 2:
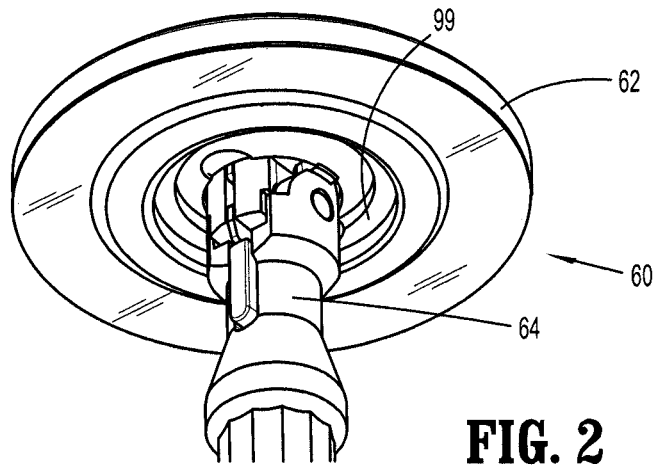
FIG. 2 is a partial, perspective view of the anvil assembly of the surgical stapling apparatus of FIG. 1.
Figure 3:
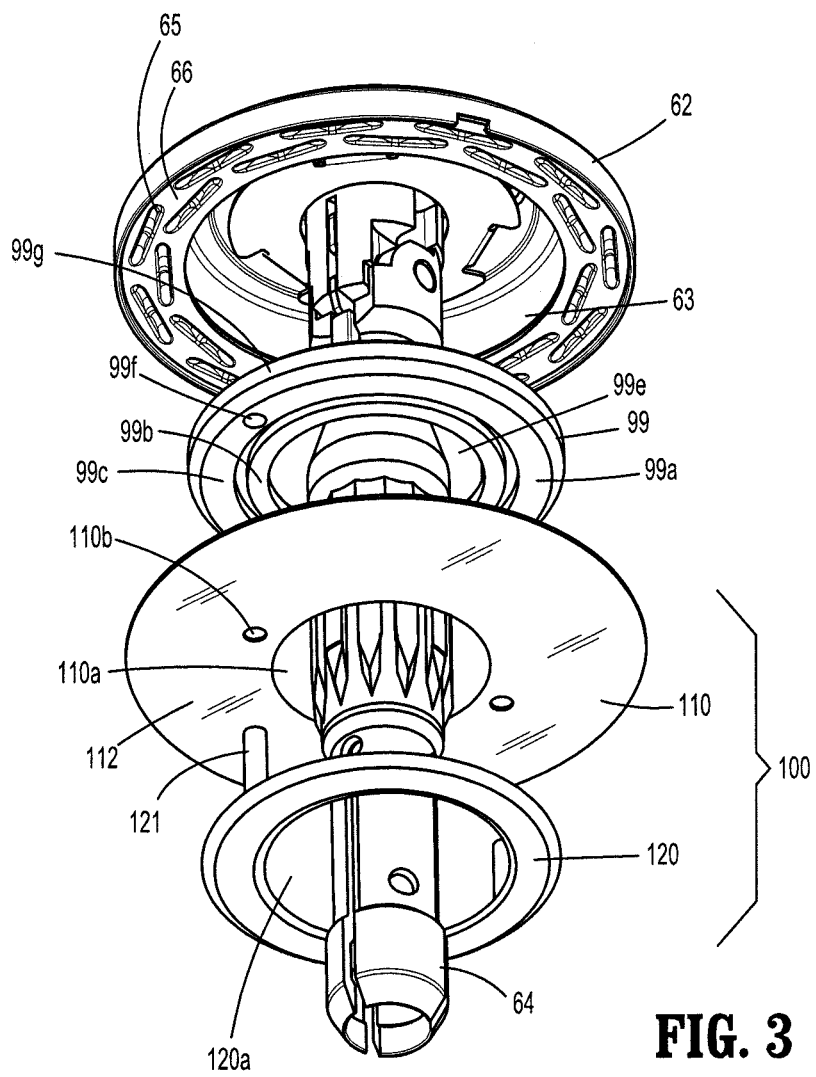
FIG. 3 is a perspective view of the surgical buttress assembly of FIG. 2 with parts separated.

With particular reference to FIGS. 2 and 3, positioned distally of staple cartridge assembly 70 is anvil assembly 60 including an anvil member 62 and a shaft 64 extending proximally from anvil member 62. Anvil member 62 includes a plurality of staple pockets 65 for receiving and deforming the staples. Shaft 64 is configured to be detachably received in approximation shaft 75 (FIG. 1) disposed in elongate body portion 30. Approximation shaft 75 is operatively coupled with rotatable grip member 26 of handle assembly 20, whereby rotation of rotatable grip member 26 moves approximation shaft 75 axially. Such axial movement of approximation shaft 75 is imparted to anvil assembly 60 detachably coupled with approximation shaft 75. In this manner, anvil assembly 60 is movable axially relative to staple cartridge assembly 70 between a spaced apart position and an approximated position in which anvil assembly 60 is positioned adjacent staple cartridge assembly 70 to adjustably clamp tissue between anvil assembly 60 and staple cartridge assembly 70.

With continued reference to FIGS. 2 and 3, surgical buttress assembly 100 includes a ring member, such as a cut ring 99, that is concentrically disposed within a recess 63 defined in anvil member 62, a buttress member 110, and a retaining member 120 concentrically arranged with buttress member 110. Cut ring 99 is configured to engage cylindrical knife 76. Buttress member 110 is provided to reinforce and seal staple lines applied to tissue by surgical stapling apparatus 10. Retaining member 120 is configured to secure buttress member 110 with anvil member 62. The ring member or cut ring resiliently engages the knife. The cut ring is desirably made from a soft plastic that the knife cuts into, and improves the quality of the cut through the tissue.

Buttress member 110 is fabricated from a biocompatible material which is bio-absorbable or non-absorbable, as well as natural or synthetic materials. It should be understood that any combination of natural, synthetic, bio-absorbable, and non-bioabsorbable materials may be used to form buttress member 110.

In addition, buttress member 110 may be porous, non-porous, or combinations thereof. It is also envisioned that buttress member 110 described herein may contain a plurality of layers in which any combination of non-porous and porous layers may be configured. For example, buttress member 110 may be formed to include multiple non-porous layers and porous layers that are stacked in an alternating manner. In another example, buttress member 110 may be formed in a "sandwich-like" manner wherein the outer layers of buttress member 110 include porous layers and the inner layers are non-porous layers. Examples of multi-layered buttress members are disclosed in U.S. Patent Application Publication No. 2009/0001122, filed on Jun. 27, 2007, entitled "Buttress and Surgical Stapling Apparatus," the entire disclosure of which is incorporated by reference therein.

In particular, the use of non-porous layers in buttress member 110 may enhance the ability of buttress member 110 to resist tears and perforations during the manufacturing, shipping, handling, and stapling processes. In addition, the use of a non-porous layer in the surgical buttress may also retard or inhibit tissue ingrowth from surrounding tissues, and thereby acting as an adhesion barrier and inhibiting the formation of unwanted scar tissue.

In addition, at least one bioactive agent may be combined with buttress member 110. The agent may be disposed on a surface of the surgical buttress and/or impregnated therein. In these embodiments, buttress member 110 can also serve as a vehicle for delivery of the bioactive agent. The term "bioactive agent," as used herein, is used in its broadest sense and includes any substance or mixture of substances that have clinical use.

With particular reference to FIG. 3, anvil member 62 includes recess 63 defined radially inward of the pair of annular arrays of staple pockets 65. Recess 63 is configured to receive cut ring 99 therein. Ring member or cut ring 99 includes a proximal surface 99a having a base portion 99b and a raised portion 99c extending proximally from base portion 99b. Raised portion 99c is disposed at a peripheral portion of cut ring 99. Cut ring 99 defines a center aperture 99e configured and dimensioned to receive shaft 64 therethrough. Raised portion 99c (FIG. 4) has a substantially flat surface (e.g., planar surface that is perpendicular to a longitudinal axis of shaft 64) configured to facilitate coring of tissue and buttress member 110 by cylindrical knife 76. When cut ring 99 is disposed within recess 63, raised portion 99c is substantially flush with proximal surface 66 of anvil member 62. Base portion 99b defines a pair of diametrically opposed bores 99f (each extending in a direction parallel to the longitudinal axis) configured to receive respective, axially extending bosses 121 extending from retaining member 120. A side wall 99g of cut ring 99 may be provided with an adhesive or friction fit configuration with recess 63 of anvil member 62 to provide securement therewith.

Figure 4:
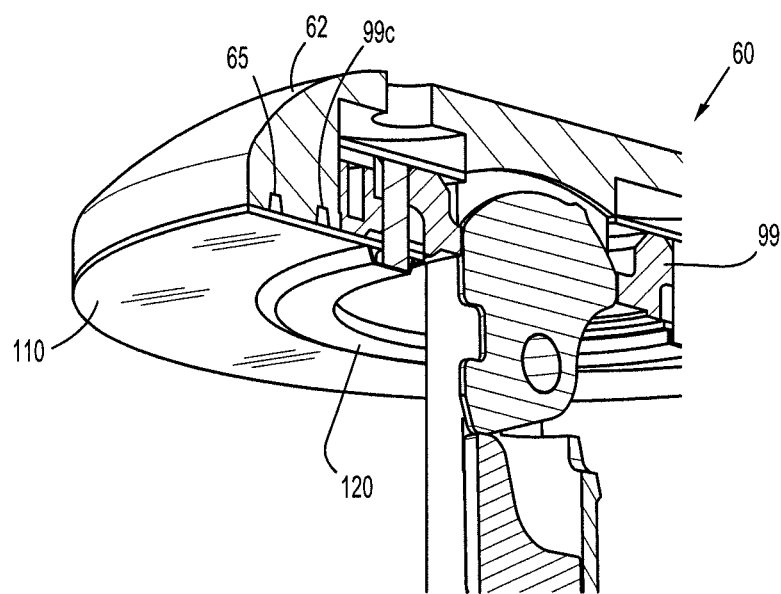
FIG. 4 is a cutaway, perspective view of the anvil assembly of FIG. 2.

With continued reference to FIGS. 2-4, buttress member 110 has an annular profile configured to be concentrically aligned with anvil member 62. Buttress member 110 is mounted on a proximal surface 66 of anvil member 62, and retaining member 120 is disposed proximal of buttress member 110. The annular profile of buttress member 110 is configured and dimensioned to at least be flush with an outer peripheral edge of anvil member 62 when mounted thereon.

Buttress member 110 defines a central aperture 110a configured to receive shaft 64 therethrough and a pair of diametrically opposing apertures 110b configured to receive the respective bosses 121 of retaining member 120. Buttress member 110 is configured and dimensioned to engage raised portion 99c of cut ring 99 and proximal surface 66 of anvil member 62. Buttress member 110 is in a superposed relation with the pair of annular arrays of staple pockets 65 defined in anvil member 62. In an embodiment, raised portion 99c of cut ring 99 may be disposed radially inward of central aperture 110a of buttress member 110 to improve securement of buttress member 110 with cut ring 99. Under such a configuration, raised portion 99c may be configured and dimensioned to be substantially flush with buttress member 110.

Retaining member 120 is configured to secure buttress member 110 to anvil assembly 60. In particular, retaining member 120 has an annular profile configured to be concentrically aligned with buttress member 110 and cut ring 99. An inner diameter of retaining member 120 is substantially identical to an inner diameter of central aperture 110a of buttress member 110. Retaining member 120 includes one or more retaining members, such as a pair of diametrically opposing bosses 121. The bosses are configured and dimensioned to be received through the respective apertures 110b of buttress member 110 and into bores 99f of cut ring 99. Bosses 121 each extend in a direction substantially parallel to the longitudinal axis of shaft 64 of anvil assembly 60.

Each of the pair of bosses 121 is fixed, e.g., heat-staked, into the respective bores 99f and apertures 110b. The bosses may also have a snap fit relationship with the bores and/or apertures. In this manner, buttress member 110 is secured with cut ring 99, which, in turn, is secured with anvil member 62. Alternatively, bores 99f and apertures 110b may be configured and dimensioned to provide a tight or friction fit interface against the respective bosses 121 to enable securement of buttress member 110 with anvil member 62. Moreover, retaining member 120 may be affixed to a proximal surface 112 of buttress member 110 by, for example, over molding, ultrasonic welding, melt pressing or melt pressing in conjunction with other polymers or with adhesives. In an embodiment, raised portion 99c of cut ring 99 may be configured and dimensioned to be received within central apertures 110a, 120a of buttress member 110 and retaining member 120, respectively, to improve securement of buttress member 110 and retaining member 120 with cut ring 99. Under such a configuration, retaining member 120 is substantially flush with raised portion 99c and extends radially outward from raised portion 99c of cut ring 99.

With particular reference now to FIG. 4, buttress member 110 is in a superposed relation with the pair of annular arrays of staple pockets 65 defined in anvil member 62. In particular, an outer diameter of retaining member 120 is smaller than an outer diameter of cut ring 99, and in particular, smaller than an outer diameter of raised portion 99c. In addition, the outer diameter of retaining member 120 is smaller than an inner diameter of cylindrical knife 76 such that severing of a portion of retaining member 120 by cylindrical knife 76 may be eliminated.

In operation, when the staples are ejected through the pair of annular arrays of staple receiving slots 72, the legs of each staple penetrate through tissue and buttress member 110 into staple pockets 65. Under such a configuration, retaining member 120 is not affected by the staple formation. In this manner, upon actuation of handle members 22, a portion of buttress member 110 is stapled with tissue to reinforce tissue, and the remaining portions of buttress member 110 and retaining member 120 are cut and detached from the portion of buttress member 110 stapled with tissue.

Figure 5:
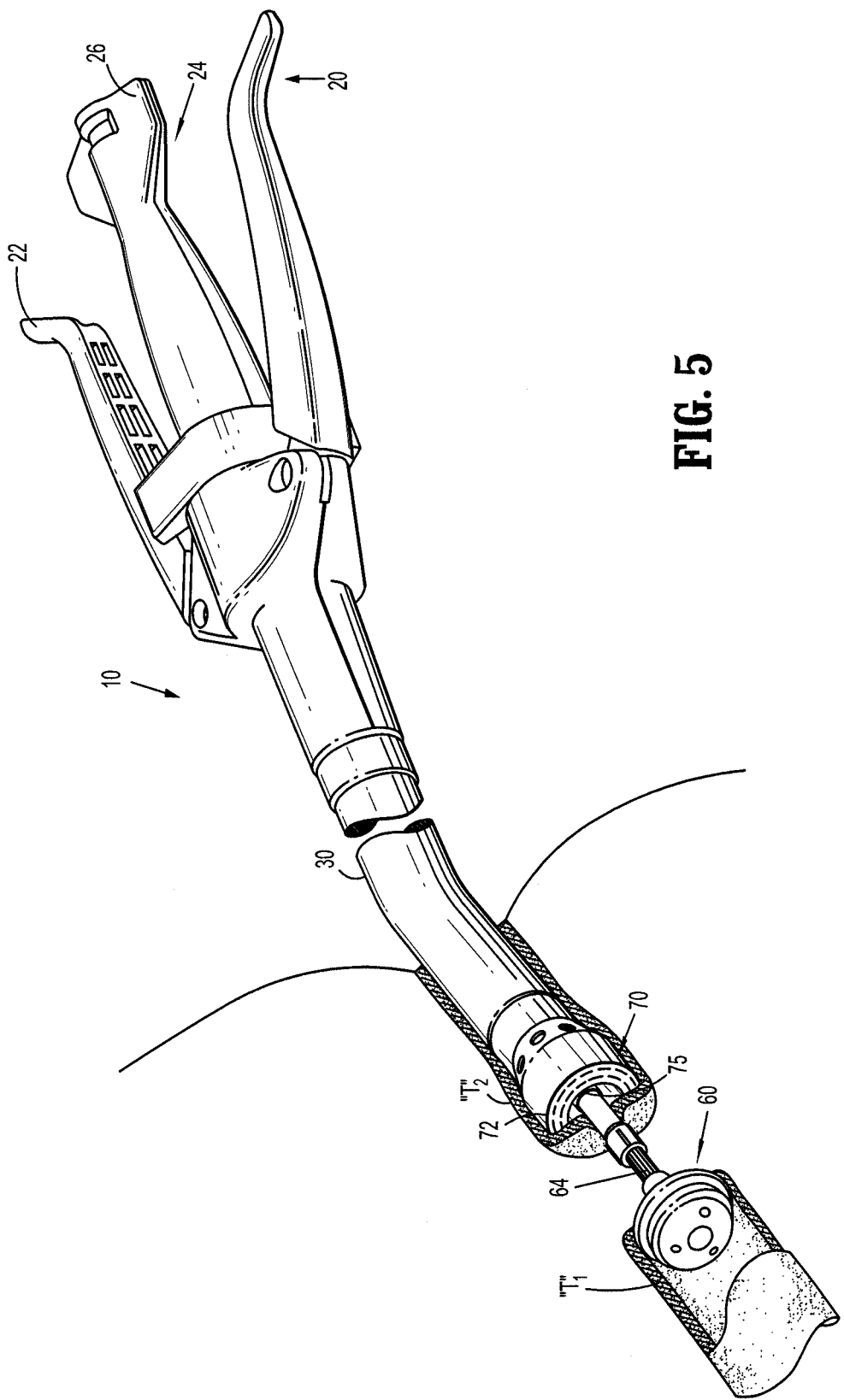
FIG. 5 is a perspective view of the annular surgical apparatus of FIG. 1, illustrating insertion of the apparatus through two hollow organ sections.

With reference now to FIG. 5, surgical stapling apparatus 10 is used in an anastomosis procedure to effect joining of, for example, two opposing intestinal sections "$T_1$," "$T_2$." The anastomosis procedure is typically performed using minimally invasive surgical techniques including laparoscopic means and instrumentation. Initially, a diseased intestinal section is removed. Thereafter, anvil assembly 60 is inserted to the operative site either through a surgical incision or transanally and is positioned within the intestinal section "T₁." Elongate body portion 30 of surgical stapling apparatus 10 including staple cartridge assembly 70 is inserted transanally into the other intestinal section "T₂." Intestinal sections "T₁," "T₂" are then temporarily secured about their respective components (e.g., shaft 64 of anvil assembly 60 and the distal end of elongate body portion 30) by conventional means such as a purse string suture "P."

Thereafter, the clinician maneuvers anvil assembly 60 until the proximal end of shaft 64 is inserted into the distal end of approximation shaft 75 disposed in elongate body portion 30 of surgical stapling apparatus 10. Shaft 64 engages approximation shaft 75 to be operable as a unitary construct. Anvil assembly 60 and elongate body portion 30 are then approximated to approximate intestinal sections "T₁," "T₂." Surgical stapling apparatus 10 is then fired, effecting stapling of intestinal sections "T₁," "T₂" to one another, while cylindrical knife 76 cuts a portion of buttress member 110 and tissue disposed radially inward of cylindrical knife 76, and thereby detaching retaining member 120 and an inner portion of buttress member 110 from the portion of buttress member 110 that is clamped (approximated) between a distal surface of staple cartridge assembly 70 and proximal surface 66 of anvil assembly 60 to complete the anastomosis.

Examples of instruments for performing circular anastomosis of hollow organs and methods of use are described in U.S. Pat. Nos. 6,053,390; 5,588,579; 5,119,983; 5,005,749; 4,646,745; 4,576,167; and 4,473,077, each of which is incorporated herein in its entirety by reference.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. An apparatus for joining two hollow organ sections, comprising:
    a staple cartridge assembly including a plurality of surgical staples in an annular array;
    an anvil assembly including an anvil member and a shaft extending therefrom, the anvil member including a proximal surface defining a plurality of staple pockets for deforming the surgical staples, the anvil assembly movable relative to the staple cartridge assembly between spaced apart and approximated positions to adjustably clamp tissue between the staple cartridge and anvil assemblies; and
    a buttress assembly including:
        a ring member configured to engage a knife member, the ring member secured with the anvil member;
        a buttress member having an annular configuration, the buttress member disposed in a superposed relation with the plurality of staple pockets defined in the anvil member; and
        a retaining member having an attaching member configured to be secured with the ring member to secure the buttress member between the ring member and the retaining member, and to position the buttress member relative to the anvil assembly, wherein the buttress member includes a bore configured and dimensioned to receive the attaching member of the retaining member therethrough.

2. The apparatus according to claim 1, wherein the proximal surface of the anvil member further defines a recess defined radially inward of the plurality of staple pockets, the recess configured and dimensioned to securely receive the ring member therein.

3. The apparatus according to claim 2, wherein the ring member is configured to engage an inner wall of the recess to provide securement of the ring member thereagainst.

4. The apparatus according to claim 1, wherein the attaching member is a boss extending distally from the retaining member.

5. The apparatus according to claim 4, wherein the ring member defines a bore configured and dimensioned to receive the boss.

6. The apparatus according to claim 5, wherein the boss is secured to the bore of the ring member through heat staking.

7. The apparatus according to claim 1, wherein the ring member includes a proximal face having a base portion and a raised portion extending proximally from the base portion, the raised portion configured and dimensioned to engage the knife member.

8. The apparatus according to claim 7, wherein the raised portion is substantially flush with the proximal surface of the anvil member.

9. The apparatus according to claim 7, wherein the raised portion is disposed at a peripheral portion of the ring member.

10. The apparatus according to claim 1, wherein the retaining member has an annular configuration.

11. The apparatus according to claim 10, wherein the retaining member is in a superposed relation with the buttress member.

12. The apparatus according to claim 11, wherein the retaining member is concentrically aligned with the anvil member.

13. The apparatus according to claim 1, wherein the retaining member is configured to engage a proximal face of the buttress member.

14. The apparatus according to claim 1, wherein the buttress member is made of a biodegradable material.

15. The apparatus according to claim 1, wherein the knife member is concentrically arranged with the plurality of surgical staples in the staple cartridge assembly, the knife member movable relative to the staple cartridge assembly, wherein the retaining member is disposed radially inward of the knife member when the knife member is actuated to engage the buttress member.

16. The apparatus according to claim 1, wherein the buttress member is concentrically aligned with the plurality of staple pockets and is interposed between the ring member and the retaining member.

17. The apparatus according to claim 1, wherein the buttress member and the ring member are concentrically arranged with each other.

18. The apparatus of claim 1, wherein a radially outer peripheral portion of the buttress member is flush with a peripheral edge of the anvil member.

* * * * *